(12) United States Patent
Merlo et al.

(10) Patent No.: US 9,434,679 B2
(45) Date of Patent: Sep. 6, 2016

(54) ALLYL-BEARING FLUORINATED IONOMERS

(71) Applicant: SOLVAY SPECIALTY POLYMERS ITALY S.P.A., Bollate (IT)

(72) Inventors: Luca Merlo, Montorfano (IT); Vito Tortelli, Milan (IT); Ivan Wlassics, Garessio (IT); Claudio Oldani, Nerviano (IT)

(73) Assignee: SOLVAY SPECIALTY POLYMERS ITALY S.P.A., Bollate (Milano) (IT)

( * ) Notice: Subject to any disclaimer, the term of this patent is extended or adjusted under 35 U.S.C. 154(b) by 0 days.

(21) Appl. No.: 14/420,708

(22) PCT Filed: Jul. 30, 2013

(86) PCT No.: PCT/EP2013/065980
§ 371 (c)(1),
(2) Date: Feb. 10, 2015

(87) PCT Pub. No.: WO2014/023611
PCT Pub. Date: Feb. 13, 2014

(65) Prior Publication Data
US 2015/0218084 A1  Aug. 6, 2015

(30) Foreign Application Priority Data

Aug. 10, 2012 (EP) .................... 12180024

(51) Int. Cl.
| | | |
|---|---|---|
| C07C 217/46 | (2006.01) | |
| C07C 41/30 | (2006.01) | |
| C07C 213/02 | (2006.01) | |
| C07C 43/17 | (2006.01) | |
| C08J 5/22 | (2006.01) | |
| C08G 65/00 | (2006.01) | |
| C08F 216/14 | (2006.01) | |

(52) U.S. Cl.
CPC .............. *C07C 217/46* (2013.01); *C07C 41/30* (2013.01); *C07C 43/17* (2013.01); *C07C 213/02* (2013.01); *C08G 65/007* (2013.01); *C08J 5/2237* (2013.01); *C08F 216/1466* (2013.01)

(58) Field of Classification Search
CPC ..... C07C 217/46; C07C 41/30; C07C 43/17; C07C 213/02; C07C 209/00; C08J 5/225; C08J 5/2237; C08F 216/1466; C08G 65/007
See application file for complete search history.

(56) References Cited

U.S. PATENT DOCUMENTS

| | | |
|---|---|---|
| 3,242,218 A | 3/1966 | Miller et al. |
| 3,665,041 A | 5/1972 | Sianesi et al. |
| 3,715,378 A | 2/1973 | Sianesi et al. |
| 4,523,039 A | 6/1985 | Lagow et al. |
| 4,789,717 A | 12/1988 | Giannetti et al. |
| 4,864,006 A | 9/1989 | Giannetti et al. |

(Continued)

FOREIGN PATENT DOCUMENTS

| | | |
|---|---|---|
| CA | 786877 A | 6/1968 |
| EP | 0148482 B1 | 3/1992 |

(Continued)

OTHER PUBLICATIONS

"Sianesi, D. et al., ""Perfluoropolyethers (PFPEs) from Perfluoroolefin Photooxidation, Fomblin® and Galden® Fluids""", Organofluorine Chemistry: Principles and Commercial Applications., Edited by Banks, R. E. et al., Plenum Publishing Corporation: New York, NY, USA,1994, p. 431-461.—Springer US".
"Wlassics, I. et al., ""Perfluoro Allyl Fluorosulfate (FAFS): A VersatileBuilding Block for New Fluoroallylic Compounds""", Molecules, 2011, vol. 16,p. 6512-6540."
Navarrini, W. et al., "Organic hypofluorites and their new role in industrial fluorine chemistry", Journal of Fluorine Chemistry. 1999, vol. 95, No. 1, p. 27-39—Elsevier Ltd.

*Primary Examiner* — Shailendra Kumar

(57) ABSTRACT

The present invention provides a fluorinated ionomer [polymer (I)] comprising recurring units derived from at least the following monomers: (i) 5 to 50% by weight of a fluorinated monomer [monomer (A)] containing at least one —$SO_2X$ functionality, preferably having the formula of $CF_2$=CF—O—$(CF_2CF(CF_3)O)_m$—$(CF_2)_nSO_2X$ (I) wherein m is 0 or 1, n is an integer between 0-10, and X is selected from F, OH, and O$^-$Me$^+$, wherein Me$^+$ indicates an alkali metal ion or an ammonium cation of formula $NR_4^-$ where each R independently represents a hydrogen atom or a monovalent organic radical selected from aliphatic radicals having from 1 to 8 carbon atoms and arylic or alicyclic radicals having from 3 to 8 carbon atoms; (ii) a non-functional fluorinated monomer [monomer (B)] having at least one ethylene unsaturation; and (iii) a fluorinated polyfunctional compound having the general formula: $(CR_1R_2$=$CFCF_2$—O$)_a$—$R_f$—$((O)_c$—CF=$CR_3R_4)_b$ (II) wherein: a is an integer equal to or larger than 1, preferably a is 1, 2, or 3; b is 0 or 1 and the sum of a and b is an integer equal to or larger than 2; c is 0 or 1; $R_1$, $R_2$, $R_3$ and $R_4$ are independently selected from F, H, alkyl, alkoxy, polyoxy alkyl, perfluoroalkyl, perfluoroalkoxy or perfluoropolyoxy alkyl, preferably F; and $R_f$ represents a hydrocarbon or fluorocarbon group having at least two carbon atoms. The low-EW perfluorinated ionomers made of polymer (I) are adapted to be processed into thin films, which are found to have superior physical stability than the existing products and are thus well suited for low humidity or high temperature electrochemical applications. Moreover, these low-EW ionomers are melt processable and have limited loss of volatile substances at their melt processing temperatures.

20 Claims, No Drawings

(56) References Cited

U.S. PATENT DOCUMENTS

| | | |
|---|---|---|
| 5,557,010 A | 9/1996 | Darst et al. |
| 7,041,409 B2 | 5/2006 | Wu et al. |
| 7,094,851 B2 | 8/2006 | Wu et al. |
| 7,208,638 B2 | 4/2007 | Vito et al. |
| 2005/0090601 A1 | 4/2005 | Dadalas et al. |
| 2005/0107518 A1 | 5/2005 | Zipplies et al. |
| 2008/0015304 A1 | 1/2008 | Hintzer et al. |
| 2010/0093878 A1* | 4/2010 | Yang ............... C08F 24/00 521/27 |
| 2010/0121012 A1 | 5/2010 | Hintzer et al. |
| 2010/0160510 A1 | 6/2010 | Aten et al. |
| 2011/0303868 A1 | 12/2011 | Sienkiewicz et al. |

FOREIGN PATENT DOCUMENTS

| | | |
|---|---|---|
| EP | 1589062 A2 | 10/2005 |
| GB | 1226566 A | 3/1971 |
| JP | 63048314 A | 3/1988 |
| WO | 8700538 A1 | 1/1987 |
| WO | 2008024601 A1 | 2/2008 |
| WO | 2008046816 A | 4/2008 |

\* cited by examiner

ALLYL-BEARING FLUORINATED IONOMERS

CROSS-REFERENCE TO RELATED APPLICATION

This application is a U.S. national stage entry under 35 U.S.C. §371 of International Application No. PCT/EP2013/065980 filed Jul. 30, 2013, which claims priority to European application No. 12180024.7 filed on Aug. 10, 2012. The entire contents of these applications are explicitly incorporated herein by this reference.

TECHNICAL FIELD

The present invention relates to fluorinated ionomers containing recurring units derived from certain allyl-ether containing polyfunctional fluoromonomers, and membranes obtained therefrom for electrochemical applications, in particular for fuel cells, electrochemical cells or electrolyzers. The present invention further relates to a method of making such fluorinated ionomers.

BACKGROUND ART (Per)fluorinated polymers containing sulfonyl fluoride functional groups are known in the prior art as precursors for a class of ion exchange (per)fluorinated polymers generally referred to as "ionomers". These ionomers are widely used as an ionically conducting material in electrochemical applications such as fuel cells, chloro-alkali cells, lithium batteries and electrodialysis, or as a solid catalyst in reactors. In these applications, the ionomer is in contact with an aqueous or polar liquid having affinity with the ionic functional groups of the ionomer, and is often made in the form of membranes or thin films to minimize its resistance to ionic transport.

Generally, to have a better efficiency in the ionomer applications, it is desirable to have a larger amount of ionic groups present in the ionomer chain. From this point of view, an important parameter used to characterize ionomers is "equivalent weight" (EW) which, as generally accepted in the art and consistently used in the present invention, refers to the weight of the polymer in acid form required to neutralize one equivalent of NaOH. Accordingly, higher EW means that there are fewer active ionic species present in the ionomer concerned, and therefore gives inferior ion exchange capability in electrochemical application. Hence, ionomers having a low EW are desirable since they give high application efficiency in theory.

However, for electrochemical applications, the use of low-EW ionomer was previously considered as unpractical. This is because, for the fluoropolymers currently known, a decrease in equivalent weight is directly associated with an increase in water retention, or swelling degree. In use, an excess water affinity of the ionomer has as a negative consequence of an excessive polymer swelling, which assumes a gelatinous state consequently losing its physical integrity. The ionomer becomes therefore mechanically unusable in all the electrochemical applications requiring a solid polymer form, such as in fuel cell devices.

Also in the applications where the ionomer is mixed with or deposited on a support material, suitable to guarantee the shape and the physical integrity of the final membrane, the ionomer must however show a sufficient physical consistency to prevent the release from the support and it must be quite insoluble in water with which it comes into contact during the use. Besides, for sulphonic fluorinated polymer suitable for making useful ionomeric membranes, the polymer/membrane must be activated before use, wherefore the chemical transformation of the precursor groups —SO$_2$F into the corresponding hydrolyzed form is necessary. The membrane activation is carried out first by contacting it with an alkaline aqueous solution and then with an acid solution. During this transformation phase, if the ionomer has a high swelling degree, it can partially or completely dissolve in the reaction medium. At this point, it is extremely difficult to recover the ionomer and separate it from the by-products of the transformation reaction.

Thus, in the prior art, to obtain a limited hydration of the ionomer for a sufficient physical integrity, fluorinated polymers having a high EW are used at the compromise of high application efficiency. An example of said ionomer is represented by the commercial product NAFION® from Dupont, which is a sulphonic fluorinated ionomer used in fuel cells and has a high EW in the order of 1,000 to 1,200, i.e. corresponding to a low concentration of sulphonic groups. Although NAFION® membranes generally demonstrate good physical integrity at room temperature, they typically require a high thickness of at least 100 µm. Besides, if these membranes are used at temperatures higher than 100° C., the water contained in the membrane, due to the limited number of hydrophilic groups —SO$_3$H and the high thickness, tends to diminish, wherefore the membrane tends to dehydrate and the membrane conductivity is drastically reduced. Consequently, the NAFION® membranes are not effectively usable at temperatures higher than 100° C.

In an attempt to circumvent this prior art limitation, EP 1589062 A (SOLVAY SOLEXIS S.P.A.) 26 Oct. 2005 discloses ionomer membranes comprising (per)fluorinated ionomers adapted for use in fuel cells under fully hydrated conditions and at temperatures higher than 100° C., including certain membranes formed of copolymers TFE/F$_2$C=CF—O—(CF$_2$)$_2$—SO$_2$F.

Additionally, efforts have been made in the art to deliver ionomer membranes for hydrogen-based fuel cells which are able to operate in so-called "dry conditions", i.e. without the need of sophisticated water management systems, and/or at temperatures up to 120° C.

Within this scenario, U.S. Pat. No. 7,094,851 (GORE ENTREPRISE HOLDINGS) 22 Aug. 2006 discloses ionomers having low EW (typically between 625 and 850 g/eq) and high conductivity (greater than 0.13 S/cm), which are capable of being processed into thin film and are well-suited for low humidity or high temperature fuel cell applications. Nevertheless, ionomers hereby described comprising recurring units derived from tetrafluoroethylene (TFE) and from a comonomer of formula (A):

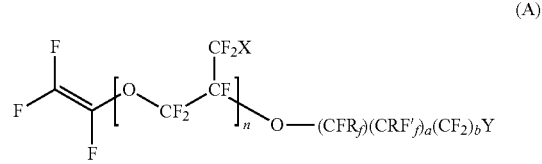

(A)

wherein X is F, Cl or Br or mixtures thereof; n is an integer equal to one or two; R$_f$ and R'$_f$ are independently selected from the group of F, Cl, perfluoroalkyl radical, and chloroperfluoroalkyl radical; Y is an acid group or a functional group convertible to an acid group, like notably —SO₃Z, with Z being H or any combination of cations; a is zero or an integer greater than zero; and b is an integer greater than zero, are known to possess poor temperature resistance, so that membranes prepared therefrom cannot withstand long-life fuel cell operations at temperatures exceeding 65° C.

Similarly, U.S. Pat. No. 7,041,409 (GORE ENTERPRISE HOLDINGS, INC.) 9 May 2006 discloses fluorinated ionomeric co-polymers comprising:
(a) a substantially fluorinated backbone;
(b) pendant groups derived from an ionomeric monomer of the formula (A)

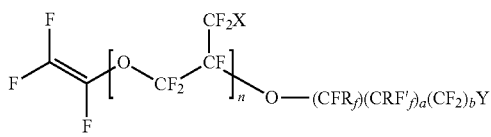

wherein X is F, Cl or Br or mixtures thereof; n is an integer from zero to two; $R_f$ and $R'_f$ are independently selected from the group of F, Cl, perfluoroalkyl radical, and chloroperfluoroalkyl radical; Y is an acid group or a functional group convertible to an acid group, like notably —SO₃Z, with Z being H or any combination of cations; a is zero or an integer greater than zero; and b is an integer greater than zero; and
(c) pendant groups derived from a vinyl ether monomer that has at least two vinyl ether groups of the form, CA₂=CB—O—, where the vinyl groups are separated by greater than four atoms; A is independently selected from the group containing F, Cl, and H; and B is independently selected from F, Cl, H and ORi, where Ri is a branched or straight chain alkane that may be partially, substantially or completely fluorinated or chlorinated, said copolymers being particularly well-suited for low humidity of high temperature fuel cell operations. Nevertheless, such ionomers were found to exhibit limited durability in high temperature PEMFC operations, due to excessive swelling.

Another similarly structured fluorinated co-polymer is mentioned in JP 63048314 A (NIPPON MEKTRON KK) 1 Mar. 1988, which is prepared by copolymerization of components (a)-(c) below:
(a) CF₂=CF—(CF₂)ₗ—O—(CF₂CF(CF₃)O)ₘ—(CF₂)ₙ—SO₂F, wherein l is 0 or 1, m is an integer between 0-2, and n is 1-4;
(b) at least one fluorinated monomer selected from tetrafluoroethylene, trifluoroethylene, perfluoropropoxypropylaryl ether, and combination thereof; and
(c) at least one fluorine-containing diene monomer selected from CF₂=CFOCF=CF₂, CF₂=CFCF₂OCF₂CF=CF₂, CF₂=CFOCF₂CF=CF₂, and combination thereof, wherein the component (a) is present in the copolymer at an amount of 0.1-10 wt %. The advantage of such copolymers, according to JP 63048314, is an improved thermal and chemical resistance for industrial uses. However, due to the particular structure of the fluorine-containing diene monomer(s) selected by JP63048314, they are highly unlikely to give crosslinking in the copolymerization process. Specifically, in a typical copolymerization process as above mentioned, a large majority of CF₂=CFCF₂OCF₂CF=CF₂ or CF₂=CFOCF₂CF=CF₂ monomers would react intramolecularly and form a ring structure of oxane or tetrahydrofuran along the polymer main chain, due to thermodynamic consideration, instead of acting as a crosslinker to react intermolecularly; and the shortest diene monomer of CF₂=CFOCF=CF₂ mentioned above is difficult to be prepared and would eventually give a very tight crosslinking due to the closeness of two double bonds in one molecule, therefore not easily adaptable for industrial uses.

Therefore, the need was felt to have new, crosslinked fluorinated ionomers such that the membranes obtained therefrom have an optimal combination of high ionic conductivity, proper hydration and good physical integrity even in extremely thin thickness, both at room temperature and higher operation temperatures without substantially compromising the membrane physical integrity, to suit most electrochemical applications.

Furthermore, it would be desirable to have available sulfonyl fluoride polymers as precursors of low-EW ionomers, which are melt processable and have no or limited loss of volatile substances at their melt processing temperatures.

The Applicant has surprisingly and unexpectedly found fluorinated ionomers able to solve the aforementioned technical problem.

SUMMARY OF INVENTION

An object of the present invention is to provide a fluorinated polymer [polymer (I)] comprising recurring units derived from at least the following monomers:
(i) 5 to 50% by weight of a fluorinated monomer [monomer (A)] containing at least one —SO₂X functionality, preferably having the formula (I): CF₂=CF—O—(CF₂CF(CF₃)O)ₘ—(CF₂)ₙSO₂X (I)
wherein m is 0 or 1, n is an integer between 0-10, and X is selected from F, OH, and O⁻Me⁺, wherein Me⁺ indicates an alkali metal ion or an ammonium cation of formula NR₄⁺ where each R independently represents a hydrogen atom or a monovalent organic radical selected from aliphatic radicals having from 1 to 8 carbon atoms and arylic or alicyclic radicals having from 3 to 8 carbon atoms;
(ii) a non-functional fluorinated monomer [monomer (B)] having at least one ethylene unsaturation; and
(iii) a fluorinated polyfunctional compound having the general formula (II):

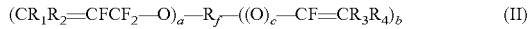

wherein: a is an integer equal to or larger than 1, preferably a is 1, 2, or 3; b is 0 or 1 and the sum of a and b is an integer equal to or larger than 2; c is 0 or 1; $R_1$, $R_2$, $R_3$ and $R_4$ are independently selected from F, H, alkyl, alkoxy, polyoxy alkyl, perfluoroalkyl, perfluoroalkoxy or perfluoropolyoxy alkyl, preferably F; and $R_f$ represents a hydrocarbon group or fluorocarbon group having at least two carbon atoms.

For the purpose of the invention, the term "hydrocarbon group" refers to a non-fluorinated group containing carbon and hydrogen atoms, as well as optional elements other than carbon and hydrogen such as oxygen, nitrogen, sulphur and silicon.

The term "fluorocarbon group" generally refers to a chemical group having carbon and fluorine atoms. As used herein, the fluorocarbon group can be saturated or unsaturated, aromatic or non-aromatic, branched or cyclic, and optionally contains a heteroatom selected from O, N and S.

The monomers of the polymer (I) can be 'functional' or 'non-functional'. In the context of the present invention, a non-functional fluorinated monomer of the polymer (I) is a monomer comprising a fluorocarbon chain and free from functional groups. As used herein, the term "functional group" has its general meaning in the organic chemistry and it encompasses atoms or combination of atoms bonded to the carbon skeleton of the fluorocarbon chain of a fluorinated monomer, which are capable to enter chemical reaction(s) as a whole. In other words, a functional group represents a potential reaction site in an organic compound and may alter the properties of the carbon skeleton it bonds to.

The fluorinated ionomers made of polymer (I) of the invention can be obtained with a relative low range of EW (e.g. lower than 1000 g/eq) compared to many commercially available ionomers, and are adaptable to be processed into thin films. The thin films made from polymer (I) are found to have superior mechanical stability compared with the existing products and enhanced chemical resistance in oxidative environment, and are thus less prone to chemical and mechanical degradation. Advantageously, the ionomers made of polymer (I) are melt processable in their —$SO_2F$ precursor form and are dispersible in (hydro)alcoholic medium in their hydrolyzed form, including the —$SO_3H$ form and —$SO_3Me$ form.

For the purpose of the present invention, the term "ionomer" is used to refer to a fluorinated polymer comprising recurring units derived from at least one ethylenically unsaturated fluorinated monomer comprising at least one ion exchange group —$SO_3^-$ and from at least one ethylenically unsaturated fluorinated monomer.

The term "fluorinated" is used herein to refer to compounds (e.g. monomers, polymers etc.) that are either totally or partially fluorinated, i.e wherein all or only a part of the hydrogen atoms have been replaced by fluorine atoms.

The polymer (I) of the present invention can be prepared from monomer (A) in its —$SO_2F$ form (i.e. when X=F), by standard methods known in the art, and comprises —$SO_2F$ functional groups.

The polymer (I) can also be obtained in its salified form and contains —$SO_2X$ functionality where $X=O^-Me^+$, by treatment of the corresponding polymer comprising —$SO_2F$ functional groups, with a strong base (e.g. NaOH, KOH).

Alternatively, the polymer (I) can be obtained in its acid form and contains —$SO_3H$ functional group, by treatment of the corresponding salified form of the polymer with a concentrated acid solution.

The polymer (I) of the present invention comprises from 5 to 50% by weight, preferably from 10 to 40% by weight, and more preferably from 15 to 35% by weight of recurring units derived from monomer (A). Still preferably, monomer (A) has formula (I): $CF_2=CF-O-(CF_2CF(CF_3)O)_m-(CF_2)_nSO_2X$ (I)

wherein m is 0 or 1, n is an integer between 0-10, and X is selected from F, OH, and $O^-Me^+$, wherein $Me^+$ indicates an alkali metal ion preferably selected from $Na^+$ and $K^+$ or, alternatively, an ammonium cation of formula $NR_4^+$ where each R independently represents a hydrogen atom or a monovalent organic radical selected from aliphatic radicals having from 1 to 8 carbon atoms and arylic or alicyclic radicals having from 3 to 8 carbon atoms.

Non limiting examples of suitable monomers (A) for the present invention are:
compounds of formula: $CF_2=CF-O-(CF_2CF(CF_3)O)_m-(CF_2)_nSO_2X$, wherein m is 0 or 1 and n is an integer between 0-10, preferably between 1 and 6 and more preferably between 2 and 4;
compounds of formula: $CF_2=CF(CF_2)_pSO_2X$ wherein p is an integer between 0 and 10, preferably between 1 and 6, more preferably p is equal to 2 or 3;
fluoroalkoxyvinylethers of formula: $CF_2=CF-(OCF_2CF(R_{F1}))_w-O-CF_2(CF(R_{F2}))_ySO_2X$ wherein w is an integer between 0 and 2, $R_{F1}$ and $R_{F2}$, equal or different from each other, are independently F, Cl or a $C_1-C_{10}$ fluoroalkyl group, optionally substituted with one or more ether oxygens, y is an integer between 0 and 6; preferably w is 1, $R_{F1}$ is —$CF_3$, y is 1 and $R_{F2}$ is F;
aromatic fluoroolefins of formula $CF_2=CF-Ar-SO_2X$ wherein Ar is a $C_5-C_{15}$ aromatic or heteroaromatic substituent.

Preferably monomer (A) is selected from the compounds of formula: $CF_2=CF-O-(CF_2CF(CF_3)O)_m-(CF_2)_nSO_2X$, wherein m is 0 or 1 and n is an integer between 0-10, preferably between 1 and 6 and more preferably between 2 and 4.

Among the more preferred examples of monomer (A) in —$SO_2F$ form, mention can be made of:

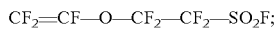

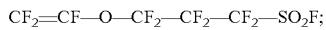

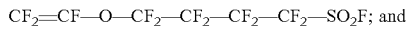

More preferably monomer (A) in —$SO_2F$ form is $CF_2=CFOCF_2CF_2-SO_2F$ (perfluoro-5-sulfonylfluoride-3-oxa-1-pentene).

Typically, polymer (I) of the present invention also comprises from 30 to 95% by weight, preferably from 45 to 90% by weight, and more preferably from 65 to 85% by weight of recurring units derived from monomer (B).

Non limiting examples of monomer (B) for the present invention include:
$C_2-C_8$ fluoroolefins, such as tetrafluoroethylene (TFE), pentafluoropropylene, hexafluoropropylene (HFP), and hexafluoroisobutylene;
vinylidene fluoride (VDF);
$C_2-C_8$ chloro- and/or bromo- and/or iodo-fluoroolefins, such as chlorotrifluoroethylene (CTFE) and bromotrifluoroethylene;
fluoroalkylvinylethers of formula $CF_2=CFOR_{f1}$, wherein $R_{f1}$ is a $C_1-C_6$ fluoroalkyl, e.g. —$CF_3$, —$C_2F_5$, —$C_3F_7$;
fluoro-oxyalkylvinylethers of formula $CF_2=CFOR_{O1}$, wherein $R_{O1}$ is a $C_1-C_{12}$ fluoro-oxyalkyl having one or more ether groups, for example perfluoro-2-propoxypropyl;
fluoroalkyloxy-difluoromethylen-vinylethers of formula $CF_2=CFOCF_2OR_{f2}$ in which $R_{f2}$ is a $C_1-C_6$ fluoroalkyl, e.g. —$CF_3$, —$C_2F_5$, —$C_3F_7$ or a $C_1-C_6$ fluorooxyalkyl having one or more ether groups, like —$C_2F_5-O-CF_3$;
fluorodioxoles, of formula:

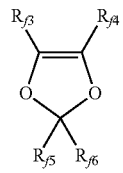

wherein each of $R_{f3}$, $R_{f4}$, $R_{f5}$, $R_{f6}$, equal or different each other, is independently a fluorine atom, a $C_1-C_6$ fluoro (halo)fluoroalkyl, optionally comprising one or more oxygen atom, e.g. —CF$_3$, —C$_2$F$_5$, —C$_3$F$_7$, —OCF$_3$, —OCF$_2$CF$_2$OCF$_3$.

Preferably, monomer (B) may be selected from:

C$_2$-C$_8$ perfluoroolefins, preferably tetrafluoroethylene (TFE) or hexafluoropropylene (HFP);

vinylidene fluoride (VDF);

C$_2$-C$_8$ chloro- and/or bromo- and/or iodo-fluoroolefines, such as -chlorotrifluoroethylene (CTFE) and bromotrifluoroethylene;

fluoroalkylvinylethers of formula CF$_2$=CFOR$_{f1}$ in which R$_{f1}$ is a C$_1$-C$_6$ fluoroalkyl, e.g. —CF$_3$, —C$_2$F$_5$, —C$_3$F$_7$;

fluoro-oxyalkylvinylethers of formula CF$_2$=CFOR$_{O1}$, in which R$_{O1}$ is a C$_1$-C$_{12}$ fluorooxyalkyl having one or more ether groups, like perfluoro-2-propoxy-propyl More preferably, polymer (I) of present invention contains TFE as monomer (B).

Typically, the polymer (I) comprises from 0.01 to 5% by weight, preferably 0.01 to 1% by weight, and more preferably from 0.02 to 0.1% by weight of recurring units derived from fluorinated polyfunctional compound of formula (II):

$$(CR_1R_2\!=\!CFCF_2\!-\!O)_a\!-\!R_f\!-\!((O)_c\!-\!CF\!=\!CR_3R_4)_b \quad (II)$$

wherein: a is an integer equal to or larger than 1, preferably a is 1, 2, or 3; b is 0 or 1 and the sum of a and b is an integer equal to or larger than 2; c is 0 or 1; R$_1$, R$_2$, R$_3$ and R$_4$ are independently selected from F, H, alkyl, alkoxy, polyoxy alkyl, perfluoroalkyl, perfluoroalkoxy or perfluoropolyoxy alkyl, preferably F; and R$_f$ represents a hydrocarbon group or fluorocarbon group having at least two carbon atoms.

According to the preferred embodiments of the present invention, in the above-described formula (II), the sum of a and b is an integer from 2 to 4. More preferably, R$_f$ represents a divalent, trivalent, or tetravalent fluorocarbon group having at least two carbon atoms and containing a backbone of perfluoroalkyl, perfluoroalkoxy or perfluoropolyoxy alkyl, optionally containing sulfonimide groups; or R$_f$ represents a divalent, trivalent, or tetravalent group having at least carbon atoms, being selected from a non-fluorinated aromatic moiety, a fluorinated aromatic moiety and a perfluorinated aromatic moiety, optionally substituted with one or more non-hydrogen substituents. The "non-hydrogen substituents" include, for example, halo, haloalkyl (preferably halo-substituted, C$_1$-C$_6$ alkyl), alkyl (preferably C$_1$-C$_6$ alkyl), alkoxy (preferably C$_1$-C$_6$ alkoxy), and the like.

Still preferably, R$_f$ is a C$_2$-C$_{20}$ alkylene or fluoroalkylene group, linear or branched, which optionally contains cyclic or aromatic moieties and/or at least one substituent selected from the group consisting of —CON(R')—, —SO$_2$N(R')—, —S—, —O—, or —N(R')— wherein R' is H or a C$_1$-C$_6$ alkylene or fluoroalkylene radical.

In specific embodiments of the present invention, R$_f$ can be selected from a group consisting of:

—(CF$_2$)$_{n'}$— with n' being an integer from 2 to 12;

—CF$_2$—O—CF$_2$—;

—CF$_2$—O—CF$_2$—CF$_2$—;

—CF(CF$_3$)—;

—(CF$_2$)$_2$—O—CF(CF$_3$)—CF$_2$—;

—CF(CF$_3$)—CF$_2$—O—CF(CF$_3$)—;

—(CF$_2$)$_2$—O—CF(CF$_3$)—CF$_2$—O—CF(CF$_3$)—CF$_2$—O—CF$_2$—;

—(CF$_2$)$_{m'}$—SO$_2$—NH—SO$_2$(CF$_2$)$_{m'}$—; and,

CH$_{4-m''}$(SO$_2$(CF$_2$)$_{m'}$)$_{m''}$—, wherein each m' is independently an integer from 1 to 12 and m'' is an integer from 1 to 3.

In a first preferred embodiment of the present invention, R$_f$ is a divalent fluorocarbon group having at least two carbon atoms and containing a backbone of perfluoroalkyl, perfluoroalkoxy or perfluoropolyoxy alkyl, which further contains at least one sulfonimide group. For instance, a preferred allyl-bearing fluorinated polyfunctional compound of formula (II) has the following structure:

$$(CF_2\!=\!CFCF_2\!-\!O\!-\!CF_2CF_2SO_2)_2NH \quad (c).$$

In one embodiment of the present invention, the allyl-bearing fluorinated polyfunctional compounds of formula (II) are selected from the compounds where R$_f$ is a perfluoropolyoxy-alkylene chain. Non limiting examples of suitable compounds in this embodiment are compounds (a) and (b) below:

$$CF_2\!=\!CF\!-\!O\text{-PFPE-}O\!-\!CF_2CF\!=\!CF_2 \quad (a); \text{ and}$$

$$(CF_2\!=\!CFCF_2\!-\!O)_2\text{-PFPE} \quad (b),$$

wherein 'PFPE' indicates a perfluoropolyether chain optionally containing functional groups (e.g. hydroxylic group, acid group, ester group, urethane methacryate, triethoxysilane, etc.).

Preferably, the molecular weight of compound (a) is between 400 and 1500, more preferably between 450 and 1000. Preferably, the molecular weight of compound (b) is between 450 and 1500, more preferably between 500 and 1000.

Preferably, compounds (a) and (b) have PFPE units selected from the following groups:

$$-\!O\!-\![CF(CF_3)CF_2O]_{b1'}(CFYO)_{b2'}\!- \quad (1)$$

wherein:

Y, equal or different at each occurrence, is selected from a fluorine atom and a —CF$_3$ group;

b1' and b2', equal to or different from each other, are independently integers ≥0 such that the b1'/b2' ratio is comprised between 20 and 1000 and the (b1'+b2') sum is comprised between 5 and 250; should b1' and b2' be both different from zero, the different recurring units are generally statistically distributed along the perfluoropolyoxyalkylene chain. Said products can be obtained by photooxidation of C$_3$F$_6$ as described in CA 786877 (MONTEDISON S.P.A.) 4 Jun. 1968 and by subsequent conversion of the end groups as described in GB 1226566 (MONTECATINI EDISON S.P.A.) 31 Mar. 1971.

$$-\!O\!-\![CF(CF_3)CF_2O]_{c1'}(C_2F_4O)_{c2'}(CFYO)_{c3'}\!- \quad (2)$$

wherein:

Y, equal or different at each occurrence, has the same meaning as defined above;

c1', c2' and c3', equal to or different from each other, are independently integers ≥0 such that the (c1'+c2'+c3') sum is comprised between 5 and 250; should at least two of c1', c2' and c3' be different from zero, the different recurring units are generally statistically distributed along the perfluoropolyoxyalkylene chain.

Said products can be manufactured by photooxidation of a mixture of C$_3$F$_6$ and C$_2$F$_4$ and subsequent treatment with fluorine as described in U.S. Pat. No. 3,665,041 (MONTE-CATINI EDISON S.P.A) 23 May 1972.

$$—O—(C_2F_4O)_{d1'}(CF_2O)_{d2'}— \quad (3)$$

wherein:

d1' and d2', equal to or different from each other, are independently integers ≥0 such that the d1'/d2' ratio is comprised between 0.1 and 5 and the (d1'+d2') sum is comprised between 5 and 250; should d1' and d2' be both different from zero, the different recurring units are generally statistically distributed along the perfluoropolyoxyalkylene chain.

Said products can be produced by photooxidation of $C_2F_4$ as reported in U.S. Pat. No. 3,715,378 (MONTECATINI EDISON S.P.A.) 6 Feb. 1973 and subsequent treatment with fluorine as described in U.S. Pat. No. 3,665,041 (MONTE-CATINI EDISON S.P.A.) 23 May 1972.

$$—O—[CF(CF_3)CF_2O]_{e'}— \quad (4)$$

wherein:

e' is an integer comprised between 5 and 250.

Said products can be prepared by ionic hexafluoropropylene epoxide oligomerization and subsequent treatment with fluorine as described in U.S. Pat. No. 3,242,218 (E. I. DU PONT DE NEMOURS AND CO.) 22 Mar. 1966.

$$—O—(CF_2CF_2O)_{f'}— \quad (5)$$

wherein:

f' is an integer comprised between 5 and 250.

Said products can be obtained by a method comprising fluorinating a polyethyleneoxide, e.g. with elemental fluorine, and optionally thermally fragmentating the so-obtained fluorinated polyethyleneoxide as reported in U.S. Pat. No. 4,523,039 (THE UNIVERSITY OF TEXAS) 11 Jun. 1985.

$$—O—(CF_2CF_2C(Hal')_2O)_{g1'}—(CF_2CF_2CH_2O)_{g2'}—(CF_2CF_2CH(Hal')O)_{g3'}— \quad (6)$$

wherein:

Hal', equal or different at each occurrence, is a halogen selected from fluorine and chlorine atoms, preferably a fluorine atom;

g1', g2', and g3', equal to or different from each other, are independently integers ≥0 such that the (g1'+g2'+g3') sum is comprised between 5 and 250; should at least two of g1', g2' and g3' be different from zero, the different recurring units are generally statistically distributed along the (per)fluoropolyoxyalkylene chain.

Said products may be prepared by ring-opening polymerizing 2,2,3,3-tetrafluorooxethane in the presence of a polymerization initiator to give a polyether comprising repeating units of the formula: $—CH_2CF_2CF_2O—$, and optionally fluorinating and/or chlorinating said polyether, as detailed in EP 148482 B (DAIKIN INDUSTRIES LTD.) 25 Mar. 1992.

$$—\{C(CF_3)_2—O—[C(R_{2f})_2]_{j1'}C(R_{2f})2-O\}_{j2'}- \quad (7)$$

wherein:

$R_{2f}$, equal or different at each occurrence, is selected from a fluorine atom and a $C_1$-$C_6$ perfluoroalkyl group;

j1' is equal to 1 or 2;

j2' is an integer comprised between 5 and 250.

Said products can be produced by the copolymerization of hexafluoroacetone with an oxygen-containing cyclic comonomer selected from ethylene oxide, propylene oxide, epoxy-butane and/or trimethylene oxide (oxethane) or substituted derivatives thereof and subsequent perfluorination of the resulting copolymer, as detailed in patent application WO 8700538 (LAGOW ET AL.) 29 Jan. 1987.

Preferably, compounds (a) and (b) have PFPE units selected from groups (1)-(3) as described above, more preferably from group (3).

The allyl-bearing fluorinated polyfunctional compounds of formula (II) are available in the art and can be prepared by any standard process. Particularly, preparation methods of these allyl-bearing compounds of formula (II) can be found in D. SIANESI, G. MARCHIONNI, et al. ORGANOFLUORINE CHEMISTRY: PRINCIPLES AND COMMERCIAL APPLICATIONS. Edited by R. E. BANKS. NEW YORK: PLENUM PRESS, 1994. p. 431. and references therein.

The fluorinated polymer (I) of the present invention can optionally be crosslinked. Preferably, the polymer (I) is used under crosslinked form in fuel cell membrane, to improve mechanical resistance, increase elastic module and reduce the undesired leaching of polymer fragments.

For the purpose of the invention, the term "crosslinked" is used to denote a polymer whose polymer chains are joined together by at least two covalent bonds; and the term "crosslinking" is used to refer to a process of covalently joining two or more polymers or segments of a polymer.

For the purpose of the invention, the term "crosslinker" or "crosslinking agent" is used herein to denote a substance that promotes crosslinking when added to a polymer, polymer composition, and the like.

Crosslinking of polymer (I) can take place by radical route. For instance, radical crosslinking of polymer (I) can take place on the carbon atoms of the allyl-bearing unit.

As regards the preparation of polymer (I) of the present invention, it can be carried out by polymerization in aqueous emulsion according to well known methods of the prior art, in the presence of radical initiators (for example, alkaline or ammonium persulphates, perphosphates, perborates or percarbonates), optionally in combination with ferrous, cupric or silver salts, or other easily oxidizable metals.

In the polymerization reaction medium also surfactants of various type are usually present, among which the fluorinated surfactants of formula: $R_f$—$X^-M^+$ are particularly preferred, wherein $R_f$ is a $C_5$-$C_{16}$ (per)fluoroalkyl chain or a (per)fluoropolyoxyalkylene chain, $X^-$ is —COO$^-$ or —SO$_3^-$, $M^+$ is selected from: $H^+$, $NH_4^+$, alkaline metal ion. Among the most commonly used we can mention: ammonium perfluoro-octanoate, (per)fluoropolyoxyalkylenes ended with one or more carboxylic groups, etc.

When the polymerization is over, the polymer (I) is isolated by conventional methods, such as coagulation by addition of electrolytes or by cooling.

Alternatively, the polymerization reaction can be carried out in bulk or in suspension, in an organic liquid wherein a suitable radical initiator is present, according to well known techniques.

The polymerization reaction is generally carried out at temperatures in the range of 25° C.-150° C., under a pressure up to 10 MPa.

The preparation of polymer (I) of the invention is preferably carried out in aqueous emulsion in the presence of an emulsion, dispersion or microemulsion of perfluoropolyoxyalkylenes, according to U.S. Pat. No. 4,789,717 B (AUSIMONT S.P.A.) 6 Dec. 1988 and U.S. Pat. No. 4,864,006 B (AUSIMONT S.P.A.) 5 Sep. 1989.

Polymer (I) of the invention may be semi-crystalline or amorphous, depending on the molar composition of the polymer (I) and the EW thereof.

The term "semi-crystalline" is intended to denote a polymer (I) which possesses a detectable melting point, while the term "amorphous polymer" is intended to mean a polymer that does not have a crystalline form. It is generally understood that a semi-crystalline polymer (I), when analyzed in its —SO—$_2$F form, possesses a heat of fusion determined according to ASTM D 3418 of advantageously at least 0.4 J/g, preferably of at least 0.5 J/g, more preferably of at least 1 J/g.

Particularly good results have been obtained when the semi-crystalline polymer (I) of the present invention had a heat of fusion of from 2 to 8 J/g. Polymers (I) complying with such requirement were found to efficiently provide for suitable membranes used in applications where high mechanical resistance and low degradation is called for, e.g. for fuel cells operating at high temperature and low humidity.

Preferred polymer (I) of the invention has an equivalent weight (EW) of from 600 to 1000 g/eq. Polymer (I) possessing an equivalent weight comprised within such range provide a suitable compromise between need of retaining generated water and thus maximizing ionic conductivity of the membrane and requirements of suitable mechanical properties at temperatures exceeding 65° C., generally up to 100-130° C.

Polymer (I) has an equivalent weight (EW) of advantageously at most 850 g/eq, preferably at most 840 g/eq, more preferably at most 820 g/eq.

Polymer (I) has an equivalent weight (EW) of advantageously at least 550 g/eq, preferably at least 630 g/eq, more preferably at least 680 g/eq.

Equivalent weight of the polymer (I) can be determined according to well-known techniques. Generally, a weighted aliquot of the polymer (I) is compression moulded to yield a film, which is first completely hydrolyzed with a KOH solution in water and then treated with nitric acid. Polymer (I) is in this way converted from the precursor ($-SO_2F$) form to the acid ($-SO_3H$) form. Equivalent weight is thus determined by titration with a base, or using FT-IR analysis of the moulded polymer film.

Additionally, the polymer (I) can be eventually chemically stabilized using standard methods described in the art, such as that disclosed in WO 2008046816 A (SOLVAY SOLEXIS) 24 Apr. 2008.

Further objects of the present invention are the supported or self-supported membranes prepared using polymer (I) of the present invention.

The membranes according to the present invention generally have a thickness ranging from 5 to 200 micrometers, preferably from 8 to 100 micrometers, still more preferably from 10 to 60 micrometers. Particularly, the Applicant has found that an ionomer membrane from 10 to 60 micrometers of the present invention is particularly advantageous since it provides a fair compromise between the required mechanical stability and water affinity for the electrochemical application such as fuel cell.

The membranes of the present invention can consist essentially of the polymer (I) as above detailed or can comprise, in addition to polymer (I), other components, such as, for instance a support.

The supported or self-supported membranes of the present invention can be obtained from the polymer (I) by the processes well-known to those skilled in the art. In particular any of extrusion-molding, casting, blow-molding, impregnation, casting, coating (e.g. roller coating, gravure coating, reverse roll coating, dip coating, spray coating and the like) process can be used for manufacturing the membrane.

Typically for supported membranes, foamed PTFE can be used as support. A PTFE support which has been found to give good results is a porous support made of expanded (or bistretched) PTFE.

For self-supported membranes made from polymers (I) of the present invention, they can be obtained by subjecting the polymer (I) melt to a molding, extrusion or calendering process to obtain a film of the desired thickness, at a desired temperature for the melting processing of the polymer (I).

The membranes of the present invention, if prepared in $-SO_2F$ form, are subjected to the activation treatment to transform the sulfonyl groups $-SO_2F$ into sulphonic groups $-SO_3H$. For example activation can be carried out in 2 steps:
  step 1: salification to transform the $-SO_2F$ form into the $-SO_3K$ form; and
  step 2: acidification to transform the $-SO_3K$ form into the $-SO_3H$ form.

For example, the aforementioned salification is carried out by immersing the membrane obtained after the cross-linking reaction of the polymer (I) in an aqueous solution containing 10% by weight of KOH at a temperature in the range 60° C.-80° C. for a time higher than 2 hours. When the salification is over, the membrane is immersed into a distilled water bath at room temperature to wash the residual KOH. The following acidification is carried out for example by placing the salified membrane in an aqueous solution containing 20% by weight of HCl or $HNO_3$ at room temperature for at least 2 hours.

The resulting membrane in the $-SO_3H$ form is found suitable to be used in fuel cell applications.

Alternatively, self-supported membranes of polymer (I) can be obtained by a solvent casting method after dissolving/dispersing the polymer (I) (typically in hydrolyzed form) in a proper solvent medium, for which case the activation process is not necessary.

DESCRIPTION OF EMBODIMENTS

The invention will be explained in more detail with reference to the following examples, of which the purpose is merely illustrative and not limiting the scope of the invention.

EXAMPLES

Characterization

Equivalent Weight Determination

A weighted aliquot of the polymer (I) is compression moulded to yield a film, which is first completely hydrolyzed with a KOH solution in water and then treated with nitric acid. Polymer (I) is in this way converted from the precursor ($-SO_2F$) form to the acid ($-SO_3H$) form. Equivalent weight is thus determined by titration with a base.

Heat of Fusion Determination

Heat of fusion of a polymer is determined by DSC following the procedure of ASTM D3418-08. As specifically provided by this standard, heat of fusion is determined from the second heating curve at a heating rate of 10° C./min, after having suppressed effects of thermal history of the sample in a first heating cycle and subsequent cooling in well-defined conditions Fluoride Emission Rate Determination A polymer sample (0.4 g) is added in a polyethylene vessel previously filled with a solution containing $Fe(NH_4)_2(SO_4)_2$ (0.05 g) and $H_2SO_4$ (0.025 g) dissolved in a 15 w/w % solution of $H_2O/H_2O_2$ (200 g). The mixture thus obtained is heated at 75° C. for 4 hours, and the polymer sample is then removed, the remaining liquid collected. Fluoride concentration in the aqueous medium is assessed via Ion-exchange Chromatography (IC) using a DIONEX ICS3000 chromatography system equipped with a DIONEX IONPACK AS14A anion-exchange column and an eluent generator providing a gradient elution from KOH/H$_2$O 10 mM to KOH/H$_2$O 70 mM.

Preparative Example 1

Synthesis of an Allyl-Bearing Fluorinated Polyfunctional Compound of Formula
CF$_2$=CFCF$_2$OCF$_2$CF$_2$O-PFPE-OCF$_2$CF$_2$OCF$_2$CF=CF$_2$ 8.81 g Anhydrous KF (151.6 mmol) and 65 mL anhydrous diglyme were charged in a 250 mL glass reactor equipped with two dropping funnels, a reflux condenser, an internal thermometer and a magnetic stirring bar therein. Air in the reactor was removed by nitrogen flux in order to create an inert reaction atmosphere. The reaction mixture was then stirred by the magnetic stirring bar at 1000 rpm and subsequently cooled in an ice-water bath until an internal temperature of 4° C. was reached. 25 g (64.1 mmol) of a perfluoropolyether diacylfluoride FOC-PFPE-COF (C2/C1 ratio in PFPE unit=3.72; EW=198 g/eq) [prepared according to D. SIANESI, G. MARCHIONNI, et al. ORGANOFLUORINE CHEMISTRY: PRINCIPLES AND COMMERCIAL APPLICATIONS. Edited by R. E. BANKS. NEW YORK: PLENUM PRESS, 1994. p. 431. and references therein] was slowly added in 10 minutes, the addition rate being carefully controlled to avoid the internal temperature exceeding 8° C. Once the FOC-PFPE-COF addition was completed, the reaction mixture was stirred for 60 minutes while the internal temperature being kept at 4° C. Then to the resulted mixture was added 34.7 g fluoroallylfluorosulfate (FAFS), CF$_2$=CFCF$_2$OSO$_2$F (150.9 mmol) prepared by reacting hexafluoropropene and sulfur trioxide (SO$_3$) in the presence of a boron (BF$_3$) catalyst [according to I. WLASSICS, et al. Perfluoro Allyl Fluorosulfate (FAFS): A Versatile Building Block for New Fluoroallylic Compounds. *Molecules.* 2011, vol. 16, p. 6512-6540.], in 15 minutes, the addition speed being carefully controlled to prevent the internal temperature from exceeding 10° C. Once the FAFS addition was completed, the mixture was again stirred at 4° C. for 60 minutes. Subsequently, the mixture was heated to room temperature and stirred for another 3 hours. The crude mixture thus obtained was washed in a separatory funnel with 300 ml distilled water, and the lower organic phase was diluted with an inert, low-boiling fluorinated solvent (CF$_3$OCFClOCF$_2$Cl; methyl adduct) [according to W. NAVARRINI, V. Tortelli, et al. Organic hypofluorites and their new role in industrial fluorine chemistry. *Journal of Fluorine Chemistry.* 1999, vol. 95, p. 27-39.]. The thus obtained organic layer was then dried over MgSO$_4$, filtered, and the solvent was evaporated under a reduced pressure. Afterwards, the dried crude organic compound was distilled keeping the PFPE distributions distilling between 76°/76 mm Hg and 98° C./38 mmHg.

CF$_2$=CFCF$_2$OCF$_2$CF$_2$O-PFPE-OCF$_2$CF$_2$OCF$_2$CF=CF$_2$ (Avg. MW=709 g/mol; Functionality=1.80; density=1.69 g/ml, C2/C1 in PFPE unit ratio=3.72) was obtained in 40 mol % Yield vs. starting FOC-PFPE-COF.

$^{19}$F-NMR (ppm): 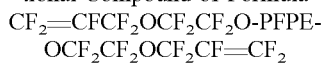O)$_2$-$^{C1}$PFPE a: −82 (2F); dd; b: −104 (2F); dd; c: −190; (2F); ddt; d: −71 (4F); s C1: −53; s; C2: −90; m.

FT-IR (cm$^{-1}$): 1792 (CF$_2$=CFCF$_2$— st); 1213 (CF st).

Preparative Example 2

Synthesis of a an Allyl-Bearing Fluorinated Polyfunctional Compound of Formula
CF$_2$=CFCF$_2$OCF$_2$CF$_2$ O-PFPE-OCF=CF$_2$ 2.11 g anhydrous KF (36.4 mmol) were suspended in 25 ml anhydrous diglyme in a 250 mL glass reactor equipped with two dropping funnels, a reflux condenser, an internal thermometer and a magnetic stirring bar. Air in the reactor was removed by nitrogen flux in order to create an inert atmosphere. The suspension was stirred at 850 rpm and cooled to 0° C. in a water/ice bath. To the cooled suspension was slowly added 26 g ClCF$_2$ CFClO-PFPE-OCF$_2$COF prepared using a mixture of perfluoropolyether diacylfluoride according to U.S. Pat. No. 7,208,638 B (SOLVAY SOLEXIS) 24 Apr. 2007, in 15 minutes, while the addition speed being carefully controlled to avoid the mixture temperature exceeding 4°-5° C. Upon the addition completion, the mixture was then stirred for 60 minutes at 0° C. 8.3 g FAFS (36.4 mmol) obtained in the same way as described in Preparative Example 1 was then slowly added in 10 minutes, and the additional speed being controlled to avoid the mixture temperature exceeding 10° C. Following the FAFS addition, the mixture was first stirred for 2 hours at 0° C. and then another hour at an increased temperature of 15° C. Afterwards, the crude mixture was poured in a separatory funnel and two separate phases were obtained immediately: a clear, colourless lower phase and a yellow top phase. The lower phase was separated, discarding the top phase which is mainly diglyme. FAFS conversion=100%. Crude adduct yield=75%

Next, 45 ml DMF and 2.96 g powdery Zn (45.5 mmol) were suspended in a glass reactor identical to the one described above, and were heated to 85° C. with stirring (1000 rpm). Into the suspension the crude adduct was slowly added within 20 minutes, during which a maximum internal temperature of 8° C. was observed. The mixture was then heated to 85°-90° C. and stirred for additional two hours at the increased temperature. Following cooling, the crude dechlorinated organic mixture was poured in a separatory funnel containing 200 ml of distilled water. The organic/water mixture was extracted with 3 portions of 50 ml CH$_2$Cl$_2$. The organic layers were then pooled together, dried over MgSO$_4$, filtered, and the solvent was evaporated under a reduced pressure. The crude oil thus obtained was distilled and the fractions distilling at 160° C./13-21 mm Hg were collected.

CF$_2$=CFCF$_2$OCF$_2$CF$_2$O-PFPE-OCF=CF$_2$ (Avg. MW=903 g/mol; Functionality=1.94; density=1.7 g/ml, b.p.=240° C., C2/C1 PFPE unit=3.38, —OCF=CF2/—OCF2CF=CF2=1.15/0.85) was obtained in 38 mol % Yield vs. starting ClCF$_2$CFClO-PFPE-OCF$_2$COF.

$^{19}$F-NMR (ppm): 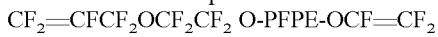CF$_2$O-$^{C1}$PFPE-O$^e$CF=$^{f,g}$CF$_2$ a: −90 (1F); dd; b: −102.5 (1F); dd; c: −188; (1F); ddt; d: −69.5 (2F); s: C1: −53; −49; s; C2: −85--89; m; e: −133.5 (1F); ddt; $^3$J$_{FF}$=65 Hz; 111 Hz; $^4$J$_{FF}$=6 Hz; f: −112.5; dd; $^2$J$_{FF}$=80 Hz; $^3$J$_{FF}$=65 Hz (1F, cis); g: −120 (1F); ddt; $^2$J$_{FF}$=84 Hz; $^3$J$_{FF}$=110 Hz (1F, trans).

FT-IR (cm$^{-1}$; KBr): 1792 (CF$_2$=CFCF$_2$O— st); 1828 (CF$_2$=CFO— st); 1193 (CF st).

Preparative Example 3

Synthesis of a an Allyl-Bearing Fluorinated Polyfunctional Compound of Formula $(CF_2=CFCF_2OCF_2CF_2SO_2)_2NH$ (a) Preparation of $BrCF_2CFBrCF_2OCF_2CF_2SO_2F$ 35 ml anhydrous $CH_3CN$ was used to dilute 16.9 g $FSO_2CF_2CF_2OCF_2CF=CF_2$ (51.2 mmol) [prepared according to I. WLASSICS, et al. Perfluoro Allyl Fluorosulfate (FAFS): A Versatile Building Block for New Fluoroallylic Compounds. *Molecules*. 2011, vol. 16, p. 6512-6540.] in a 250 ml glass reactor equipped with a dropping funnel, a reflux condenser, an internal thermometer and a magnetic stirring bar. Air in the reactor was removed by nitrogen flux in order to create an inert atmosphere. The homogeneous solution was stirred at 750 rpm and heated to 80° C. in an oil bath, after which a homogeneous solution of $CH_3CN$ (20 ml) and $Br_2$ (13.1 g; 81.94 mmol) was slowly added therein, in 25 minutes. The mixture was then stirred at 80° C. for 8 hours. The crude organic solution was washed with 30 ml of 10% (w/v) solution of $Na_2S_2O_3$ in 150 ml $H_2O$. A yellow-coloured oil phase separated at the bottom layer was collected, diluted in 50 ml $CH_2Cl_2$, dried over $MgSO_4$ and filtered, and the solvent was evaporated under a reduced pressure.

$BrCF_2CFBrCF_2OCF_2CF_2SO_2F$ was obtained with 100% selectivity and 68 mol % yield vs. $FSO_2CF_2CF_2OCF_2CF=CF_2$, of which the conversion rate is 100%.

$^{19}$F-NMR (ppm): $Br^aCF_2^bCFBr^cCF_2O^dCF_2^eCF_2SO_2^fF$ a: -55; (2F); (AB); b: -131 (1F); s; c: -72 (AB); (2F); d: -79.5 (2F); s; e: -109 (2F) s; f: 49.4 (1F); s.

(b) Preparation of $BrCF_2CFBrCF_2OCF_2CF_2SO_2NH_2$ 1.7 g liquid $NH_3$ (97.9 mmol) was obtained by condensing $NH_3$ in a vessel at -78° C. by flowing in said vessel a gaseous stream obtained by heating $NH_4OH$ at 60° C. under a slight flux of $N_2$. The -78° C. vessel containing $NH_3$ (liq.) was connected by means of PTFE tubing to a reflux condenser, which was equipped with a latex balloon at its off-gas exit port and was also cooled to -78° C. Said reflux condenser was attached to the top of a 100 mL glass reactor equipped with a dropping funnel, an internal thermometer, and a magnetic stirring bar. Air in the reactor was removed by nitrogen flux in order to create an inert atmosphere. The reactor was at 20° C. and was loaded with 8.0 g (16.34 mmol) of $BrCF_2CFBrCF_2OCF_2CF_2SO_2F$ diluted in 50 ml $CF_3OCFClCF_2Cl$. The vessel with $NH_3$ (liq.) was slowly warmed to room temperature, thereby condensing $NH_3$ (liq.) inside the reactor. The internal reactor temperature dropped to -10° C. after condensation and was subsequently heated to room temperature by immersing it in an oil bath at 50° C. As the reaction proceeded, a yellow-orange solid ($NH_4F$) formed along the sides of the reactor and the reflux rate on the reflux condenser was observed to slow down. The reactor was heated externally until the internal temperature approached the external temperature, which was an indicator that [$NH_3$] was lowering and that the reaction was over. The reflux condenser was re-heated to room temperature, the oil bath was removed from under the reactor, and stirring was maintained until no refluxing was observed and all excess $NH_3$ (gas) entered the latex balloon. The crude mixture was then diluted in another 50 ml $CF_3OCFClCF_2Cl$ and the diluted mixture was then poured in 250 ml $H_2O$, resulting separation of two homogeneous phases. The pH value of the top aqueous phase was measured to be 7.8. It was titrated to pH value of 1.8 with 20 ml of HCl (37% w/w). The lower organic phase was separated, dried over MgSO4, filtered and the solvent was evaporated under reduced pressure. The reddish, oily residue crystallized to give needle-shaped crystals at 20° C. in 2 hours.

$BrCF_2CFBrCF_2OCF_2CF_2SO_2NH_2$ was obtained in 58 mol % Yield, with a respective conversion of 97.5%.

$^{19}$F-NMR (ppm): $Br^aCF_2^bCFBr^cCF_2O^dCF_2^eCF_2SO_2NH_2$ a: -55 (AB); (2F); b: -130.8 (1F); s; c: -72.5 (AB); (2F); d: -78.7 (m); (2F); e: -114.3 (s), (2F). FT-IR (cm$^{-1}$; KBr): 1535 (—SO2-NH2 st); 3388.6, 3274.7 (—NH2 st); 1201 (CF st).

(c) Preparation of $(BrCF_2CFBrCF_2OCF_2CF_2SO_2)_2NH$ 4.64 g of $BrCF_2CFBrCF_2OCF_2CF_2SO_2F$ (9.47 mmol) and 4.61 g $BrCF_2CFBrCF_2OCF_2CF_2SO_2NH_2$ (9.47 mmol) were placed in a 100 ml glass reactor equipped with a dropping funnel, an internal thermometer and a magnetic stirring bar, and the reactor was connected to a reflux condenser having a latex balloon connected to its top off-gas exit port. Air in the reactor was removed by nitrogen flux in order to create an inert atmosphere. Into the reactor was added 35 ml of anhydrous $CH_3CN$, and the homogeneous solution was stirred at 900 rpm at 20° C. Next, 2.14 g tetramethyl guanidine (18.63 mmol) was slowly added in the reactor and 11° C. exothermicity was recorded. Tetramethyl guanidinium fluoride salt was observed to precipitate out of solution. The thus obtained crude mixture was measured to have a pH value of 11.9 and it was titrated to pH ~1 with 1 ml of 37% HCl (w/w). The titrated, acidic crude mixture was then washed with 150 ml $H_2O$. An orange-colour solid precipitated out of solution, which was diluted in 50 ml $CH_2Cl_2$. The homogeneous organic mixture was then dried over MgSO4, filtered, and the solvent was evaporated under a reduced pressure. A dark-yellow coloured oil was obtained.

$(BrCF_2CFBrCF_2OCF_2CF_2SO_2)_2NH$ was obtained in 99% Yield, with a selectivity of 99%.

$^{19}$F-NMR (ppm): $(Br^aCF_2^bCFBr^cCF_2O^dCF_2^eCF_2SO_2)_2NH$ a: -58 (AB); (4F); b: -133.6 (2F); s; c: -81.3 (AB); (4F); d: -75.6 (AB); (4F); e: -116.5 (s), (4F). FT-IR (cm$^{-1}$; KBr): 1526; 1573, 1475 (—SO2-NH2 st); 3353 (—NH st); 1993 (CF st).

(d) Preparation of $(CF_2=CFCF_2OCF_2CF_2SO_2)_2NH$ 1.796 g of powdery Zn (28.35 mmol) was suspended in 50 ml anhydrous DMF in a 100 ml glass reactor equipped with a dropping funnel, an internal thermometer and a magnetic stirring bar, the reactor being connected with a reflux condenser having a latex balloon connected to its top off-gas exit port. Air in the reactor was removed by nitrogen flux in order to create an inert atmosphere. The heterogeneous mixture was heated to 80° C. and was stirred at a speed of 1000 rpm. 9.08 g $(BrCF_2CFBrCF_2OCF_2CF_2SO_2)_2NH$ (9.5 mmol; 19 meq) was diluted in 10 ml of anhydrous DMF, placed in the dropping funnel and slowly added to the Zn suspension. During the addition an exothermicity of 7° C. was observed, which lasted for about 40 minutes as the duration of the debromination reaction. The mixture was stirred at 80° C. for another 2 hours after the exothermicity dropped. At the end of the reaction, the crude organics were placed in a separatory funnel containing 350 ml $H_2O$ acidified with 10 ml 37% HCl (w/w). A yellow-coloured oil very slowly separated to the bottom layer. The oil was first diluted in 50 ml $CH_2Cl_2$, and then retro-extracted with 100 ml $H_2O$ to remove residual tetraguanidinium salts from the previous reaction. The homogeneous organic mixture was dried over $MgSO_4$, filtered, and the solvent was evaporated under a reduced pressure.

$(CF_2=CFCF_2OCF_2CF_2SO_2)_2NH$ was obtained in 74 mol % Yield, with a density measured to be 1.633 g/ml.

$^{19}$F-NMR (ppm; DMSO d6): $(^{a,b}CF_2={}^cCF^dCF_2O^eCF_2{}^fCF_2SO_2)_2N^gH$ a: −92 dd (2F); b: −104, dd (2F); c: −190, ddt (2F); d: −72 s (4F); e: −81, m (4F); f: −117 s, (4F). 1H-NMR (ppm; DMSO d6) g: 3.3 (broad).

FT-IR (cm$^{-1}$; KBr): 1793 (CF2=CFCF2O— st.); 1328 (—SO2-NH st); 3482 (NH st).

Preparative Example 4

(Comparative): Synthesis of a Vinyl-Bearing Fluorinated Compound of Formula $CF_2=CF-O-(CF_2CF_2)_2-O-CF=CF_2$ (a) Synthesis of $ClCF_2CFClOCF_2CF_2I$ ("Compound A")

800 ml H$_2$O and 250 ml dioxane were placed in a round-bottomed flask glass reactor and were stirred at 750 rpm, at 20° C. for 20 minutes, whilst using nitrogen to inert the atmosphere. Next, 754 g Na$_2$SO$_3$ (5.98 mol) was added in the reactor and dissolved in the aqueous layer. The reducing mixture was then heated to 60° C. by means of an oil bath and 700 g of $ClCF_2CFClO-CF_2CF_2SO_2F$ (2 mol; "1") was slowly added (using 30 min) from a dripping funnel. Exothermicity was observed to have a maximum of 20° C. increase. Following the addition of 1, the reaction temperature was maintained at 80° C. for 5 hours. Afterwards, the crude mixture was cooled, the precipitate was removed by filtration and both dioxane and H$_2$O were evaporated at 50° C. and a reduced pressure. The resulting solid was washed with 800 ml isopropanol, in order to remove residual inorganic salts. The mixture was filtered and the solid was dried in an oven at 40° C. at a reduced pressure.

560 g of sulfinate (ClCF$_2$CFClOCF$_2$CF$_2$SO$_2$Na; 1.57 mol; "2") was placed in a round bottomed flask glass reactor equipped with a gas bubble counter, together with 399 g of I$_2$ (1.57 mol) and 800 ml of CH$_3$CN used as solvent. The mixture was then heated to 55° C. with stirring at 800 rpm. After 5 hours no more gas bubbles (SO$_2$) were observed at the exit port of the bubble counter, an indicator that the reaction was complete. The crude mixture was first stripped with a Claisen condenser and the crude distillate was firstly washed twice with a 10% Na$_2$SO$_3$ aqueous solution and the organic layer was further washed with a 10% NaCl aqueous solution, to remove the residual CH$_3$CN. The organic layer was dissolved in CH$_2$Cl$_2$, dried over MgSO$_4$, filtered, and the solvent was removed under reduced pressure.

ClCF$_2$CFClOCF$_2$CF$_2$I was obtained in 62 mol % Yield, with a 100% conversion vs. 1 and a 81% conversion vs. 2.

$^{19}$F NMR (ppm): $Cl^aCF_2{}^bCFClO^cCF_2{}^dCF_2I$ a: −64.5 (AB, 2F); b: −71 (s; 1F); c: −81 (AB; 2F); d: −62 (s; 2F).

(b) Synthesis of $[ClCF_2CFClOCF_2CF_2]_2$ ("Compound B")

60 g of Zinc (920 mmol), 500 ml CH$_2$Cl$_2$, and 156 g acetic anhydride (1.52 mol) were placed in a round-bottomed flask glass reactor and were stirred at 750 rpm, at 20° C. for 20 minutes, whilst using nitrogen to inert the atmosphere. Next, 300 g of Compound A (759 mmol) were dripped at 20° C., during which an exothermicity of 10° C. was observed. Once the addition of Compound A was finished, the internal reaction temperature was raised to 40°-45° C. (CH$_2$Cl$_2$ reflux) by an oil bath. A white precipitate of ZnI$_2$ formed after 6 hours. The crude mixture was first cooled, filtered to remove ZnI$_2$, and washed with 10% NaOH aqueous solution to remove acetic acid, and then the organic layer was stripped under a reduced pressure at 20° C. to remove most of residual CH$_2$Cl$_2$. Spalt-Rohr Fischer (60 theoretical plates) distillation of the stripped organic layer gave the desired product "Compound B".

Compound B (b.p.: 60° C./10 mm Hg=180° C./760 Torr.) was obtained in 70 mol % Yield, with a 100% conversion vs. Compound A.

$^{19}$F NMR (ppm): $[Cl^aCF_2{}^bCFClO^cCF_2{}^dCF_2]_2$ a: −69.5 (AB, 4F); b: −76 (s; 2F); c: −83 (AB; 4F); d: −124.5 (s; 4F).

(c) Synthesis of $[CF_2=CFOCF2CF_2]_2$ ("Compound C")

35.8 g Zinc (550 mmol), 250 ml DMF and 4 g of ZnCl$_2$ were placed in a round-bottomed flask glass reactor and were stirred at 900 rpm, at 20° C. for 20 minutes, whilst using nitrogen to inert the atmosphere. The heterogeneous mixture was heated to 80° C. in an oil bath for 30 min. Then, 106 g of compound B was slowly added from a dripping funnel, during which a peak exothermicity of 15° C. was observed. The mixture was continuously stirred at 85° C.-90° C. for 2 hours, after which the conversion is complete with concomitant generation of a white precipitate of ZnCl$_2$. Claisen distillation at 50° C. and a 60 mm Hg residual pressure gave crude Compound C, which was then distilled at the Spalt-Rohr Fischer (60 theoretical plates) to obtain pure Compound C.

Compound C (b.p.=116° C.-117° C./760 Torr.) was obtained in 90 mol % Yield with a 100% conversion vs. Compound B, giving an overall Yield of 40 mol %.

$^{19}$F NMR (ppm): $[^{a,b}CF_2={}^cCFO^dCF_2{}^eCF_2]_2$ a: −111.5; dd; $^2J_{FF}$=80 Hz; $^3J_{FF}$=65 Hz (2F, cis); b: −118.5 (2F); ddt; $^2J_{FF}$=84 Hz; $^3J_{FF}$=110 Hz (1F, trans); c: −133.5 (2F); ddt; $^3J_{FF}$=65 Hz; 111 Hz; $^4J_{FF}$=6 Hz; d: −81; s; 4F; e: −121; s; 4F.

Example 1

Fluorinated Polymer ("P1") Prepared from the Allyl-Bearing Fluorinated Polyfunctional Compound of Preparative Example 1 ("Crosslinker 1")

In a 5 L autoclave the following reagents were charged:
2.6 L of demineralised water;
145 g of the monomer with formula: $CF_2=CF-O-CF_2CF_2-SO_2F$
720 g of a 5 wt % aqueous solution of $CF_2ClO(CF_2CF(CF_3)O)_n(CF_2O)_mCF_2COOK$ (avg. MW=521, ratio n/m=10);
1 ml of a solution containing the crosslinker 1 $CF_2=CFCF_2OCF_2CF_2O$-PFPE-$OCF_2CF_2OCF_2CF=CF_2$ (5% by volume) dissolved in Galden® PFPE D02

The autoclave, stirred at 650 rpm, was heated at 50° C. A water based solution with 27 g/L of potassium persulfate was added in a quantity of 66 mL. The pressure was maintained at a value of 8 bar (abs.) by feeding tetrafluoroethylene.

After adding 40 g of tetrafluoroethylene in the reactor, 40 g of the monomer $CF_2=CF-O-CF_2CF_2-SO_2F$ and 1 ml of the crosslinker 1 dissolved in Galden® PFPE D02 (5% by volume) were added every 40 g of tetrafluoroethylene fed to the autoclave.

The reaction was stopped after 300 min by stopping the stirring, cooling the autoclave and reducing the internal pressure by venting the tetrafluoroethylene; a total of 800 g of tetrafluoroethylene was fed into the autoclave.

The latex was then coagulated by freezing and thawing and the recovered polymer was washed with water and dried at 150° C. for 24 hours.

Equivalent weight (EW) of the polymer was determined by titration to be 741 g/eq.

Heat of fusion of the polymer was determined to be 4.04 J/g.

Example 2

Fluorinated Polymer ("P2") Prepared from the Allyl-Bearing Fluorinated Polyfunctional Compound of Preparative Example 2 ("Crosslinker 2")

Example 1 was repeated except that the 1 ml solution containing the crosslinker 1 (5% by volume) dissolved in Galden® PFPE D02 was replaced by 1 ml solution containing a crosslinker 2 (11% by volume) in Galden® PFPE D02.

Equivalent weight of the polymer was determined to be 693 g/eq.

Heat of fusion of the polymer was determined to be 2.05 J/g.

Example 3

Fluorinated Polymer ("P3") Prepared from the Allyl-Bearing Fluorinated Polyfunctional Compound of Preparative Example 3 ("Crosslinker 3")

Example 1 was repeated except that the 1 ml solution containing the crosslinker 1 (5% by volume) dissolved in Galden® PFPE D02 was replaced by 1 ml solution containing a crosslinker 3 (8.5% by volume) in Galden® PFPE D02.

Equivalent weight of the polymer was determined to be 747 g/eq.

Heat of fusion of the polymer was determined to be 2.96 J/g.

Noticeably, polymers P1-P3 of the present invention each has a relative low range of EW (i.e. from 650 to 750) compared to many commercially existing ionomers, such as the aforementioned NAFION® from Dupont (whose EW is typically in the range of 1000 to 1200), and therefore provides a desirably high ion exchange capability in electrochemical applications. Moreover, polymers P1-P3 are each characterized by a heat of fusion from 2 to 8 J/g, indicative of their semi-crystalline structure and showing that the polymers are advantageously melt processable.

Comparative Example 4

Fluorinated Polymer ("P4") Prepared from the Vinyl-Bearing Fluorinated Compound of Preparative Example 4 ("Crosslinker 4")

Example 1 was repeated except that:
the 1 ml solution containing the crosslinker 1 (5% by volume) dissolved in Galden® PFPE D02 was replaced by 1 ml solution containing a vinyl-bearing crosslinker 4 (5% by volume) in Galden® PFPE D02; and
the reaction was stopped after 350 minutes by stopping the stirring.

Equivalent weight of the polymer was determined to be 740 g/eq.

Comparative Example 5

Fluorinated Polymer ("P5") Prepared from a Bis-Olefin Crosslinking Agent of $CH_2$=CH—$(CF_2)_6$—CH=$CH_2$ Example 1 was repeated except that the 1 ml solution containing the crosslinker 1 (5% by volume) dissolved in Galden® PFPE D02 was replaced by 1 ml solution containing a bis-olefin crosslinker (5% by volume) of $CH_2$=CH—$(CF_2)_6$—CH=$CH_2$ in Galden® PFPE D02.

Equivalent weight of the polymer was determined to be 751 g/eq.

Example 6

Manufacture of a Membrane Specimen from P1

9 g of polymer powder of P1 was molten between two PTFE sheets in a preheated press following the steps described below:
(1) 5 minutes of heating at 280° C. with no pressure applied;
(2) 1 minute of degassing at 280° C., with a pressure of 0.11 $kN/cm^2$ applied;
(3) 3 minutes of heating at 280° C., with a pressure of 0.15 $kN/cm^2$ applied; and;
(4) Cooling down at room temperature for 20 minutes, The membrane specimens thus obtained has a thickness of 200 micron, with no presence of bubbles detected.

0.4 g of the specimen sample thus obtained was then subjected to fluoride emission determination as described above, and was determined have a Fluoride Emission Rate (FER) of 0.115 $mg_F/g_{sample}$.

Examples 7-10

Manufacture of Membrane Specimens from P2-P5

Membranes prepared from P2-P5 were obtained using the same procedure described in Example 6, and each with the Fluoride Emission Rate (FER) determined, as listed in the table below.

TABLE 1

Fluoride Emission Rate of crosslinked fluorinated ionomers

| Sample Polymer | Polymer EW [g/mol] | FER* [$mg_F/g_{sample}$] | Crosslinker Structure |
|---|---|---|---|
| P1 | 741 | 0.115 (0.021) | $(CF_2$=$CFCF_2O)_2$—PFPE |
| P2 | 693 | 0.175 (0.007) | $CF_2$=$CFCF_2O$—PFPE—OCF=$CF_2$ |
| P3 | 747 | 0.147 (0.016) | $(CF_2$=$CFCF_2OCF_2CF_2SO_2)_2NH$ |
| P4 (comp.) | 740 | 0.162 (0.011) | $CF_2$=$CFO(CF_2)_4OCF$=$CF_2$ |
| P5 (comp.) | 751 | 0.245 (0.049) | $CH_2$=CH—$(CF_2)_6$—CH=$CH_2$ |

*The FER value was expressed in the form of AVG. (SD)

Noticeably, as shown in Table 1, all three membranes prepared from the ionomers of the present invention (P1-P3) showed superior resistance to chemical degradation in oxidative environment, especially compared to the specimen prepared from the bis-olefin crosslinker (P5). In this aspect, even comparing to the specimen prepared from the vinyl-bearing crosslinking agent (P4), the polymers of the prevent invention showed better results (P1 and P3), or at least statistically indistinguishable (P2).

This high chemical stability of the polymer of the present invention, added to its intrinsic mechanical stability induced by the crosslinking, advantageously allows one to make polymer membranes of longer lifetime and consequently broaden its application in many industrial fields.

Without wishing to be bound by theory, the Applicant believes that he introduction as comonomer of the allyl-bearing fluorinated polyfunctional compounds of formula (II) is advantageous since the particular structure of said comonomer promote pre-crosslinking of the ionomer during the polymerization, and also advantageously increases the length of the primary chains forming the final polymer without introducing in the molecular structure any weak point when subjected to chemical degradation in fuel cell environment.

The invention claimed is:

1. A fluorinated polymer (I) comprising recurring units derived from at least the following monomers:
   (i) 5 to 50% by weight of a fluorinated monomer (A) containing at least one —SO$_2$X functionality wherein X is selected from F, OH, and O$^-$Me$^+$, wherein Me$^+$ indicates an alkali metal ion or an ammonium cation of formula NR$_4^+$ where each R independently represents a hydrogen atom or a monovalent organic radical selected from aliphatic radicals having from 1 to 8 carbon atoms and arylic or alicyclic radicals having from 3 to 8 carbon atoms;
   (ii) a non-functional fluorinated monomer (B), wherein monomer (B) comprises a fluorocarbon chain having a carbon skeleton, is free from functional groups that represent potential reaction sites in an organic compound and that may alter the properties of the carbon skeleton, and has at least one ethylene unsaturation; and
   (iii) a fluorinated polyfunctional compound of formula (II):

(CR$_1$R$_2$=CFCF$_2$—O)$_a$—R$_f$—((O)$_c$—CF=CR$_3$R$_4$)$_b$     (II)

wherein: a is 1, 2 or 3; b is 0 or 1 and the sum of a and b is an integer equal to or larger than 2; c is 0 or 1; R$_1$, R$_2$, R$_3$ and R$_4$ are independently selected from F, H, alkyl, alkoxy, polyoxy alkyl, perfluoroalkyl, perfluoroalkoxy or perfluoropolyoxy alkyl; and R$_f$ represents a hydrocarbon group or fluorocarbon group having at least two carbon atoms, wherein the hydrocarbon group refers to a non-fluorinated group containing carbon and hydrogen atoms, and wherein the fluorocarbon group refers to a chemical group having carbon and fluorine atoms.

2. The polymer (I) of claim 1, wherein polymer (I) comprises from 5 to 50% by weight of recurring units derived from monomer (A).

3. The polymer (I) of claim 1, wherein monomer (A) is selected from:
   compounds of formula: CF$_2$=CF—O—(CF$_2$CF(CF$_3$)O)$_m$ —(CF$_2$)$_n$SO$_2$X, wherein m is 0 or 1 and n is an integer between 0-10;
   compounds of formula: CF$_2$=CF(CF$_2$)$_p$SO$_2$X wherein p is an integer between 0 and 10;
   fluoroalkoxyvinylethers of formula: CF$_2$=CF—(OCF$_2$CF(R$_{F1}$))$_w$—O—CF$_2$(CF(R$_{F2}$))$_y$SO$_2$X wherein w is an integer between 0 and 2, R$_{F1}$ and R$_{F2}$, equal or different from each other, are independently F, Cl or a C$_1$-C$_{10}$ fluoroalkyl group, optionally substituted with one or more ether oxygens, y is an integer between 0 and 6;
   aromatic fluoroolefins of formula CF$_2$=CF-Ar-SO$_2$X wherein Ar is a C$_5$-C$_{15}$ aromatic or heteroaromatic substituent.

4. The polymer (I) according to claim 1, wherein monomer (A) is selected from the group of compounds of formula: CF$_2$=CF—O—(CF$_2$CF(CF$_3$)O)$_m$—(CF$_2$)$_n$—SO$_2$X, wherein m is 0 or 1 and n is an integer between 0-10.

5. The polymer (I) according to claim 1, wherein monomer (A) in —SO$_2$F form is selected from the group consisting of:

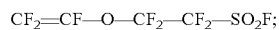

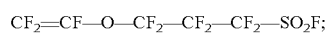

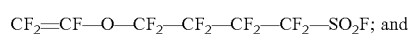

6. The polymer (I) according to claim 1, wherein polymer (I) comprises from 30 to 95% by weight of recurring units derived from monomer (B).

7. The polymer (I) according to claim 1, wherein monomer (B) is selected from the group consisting of:
   C$_2$-C$_8$ perfluoroolefins;
   vinylidene fluoride (VDF);
   C$_2$-C$_8$ chloro- and/or bromo- and/or iodo-fluoroolefines;
   fluoroalkylvinylethers of formula CF$_2$=CFOR$_{f1}$ in which R$_{f1}$ is a C$_1$-C$_6$ fluoroalkyl; and
   fluoro-oxyalkylvinylethers of formula CF$_2$=CFOR$_{O1}$, in which R$_{O1}$ is a C$_1$-C$_{12}$ fluorooxyalkyl having one or more ether groups.

8. The polymer (I) according to claim 1, wherein monomer (B) is TFE.

9. The polymer (I) according to claim 1, wherein polymer (I) comprises from 0.01 to 5% by weight of recurring units derived from fluorinated polyfunctional compound of formula (II).

10. The polymer (I) according to claim 1, wherein in said formula (II), the sum of a and b is an integer from 2 to 4, and wherein R$_f$ represents a divalent, trivalent, or tetravalent fluorocarbon group having at least two carbon atoms and containing a backbone of perfluoroalkyl, perfluoroalkoxy or perfluoropolyoxy alkyl, optionally containing sulfonimide groups; or R$_f$ represents a divalent, trivalent, or tetravalent group having at least two carbon atoms, being selected from a non-fluorinated aromatic moiety, a fluorinated aromatic moiety and a perfluorinated aromatic moiety, optionally substituted with one or more nonhydrogen substituents.

11. The polymer (I) according to claim 1, wherein R$_f$ is selected from the group consisting of:

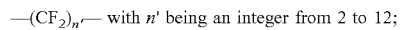

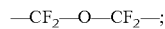

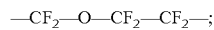

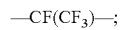

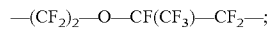

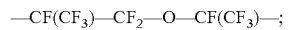

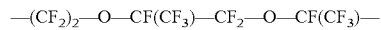

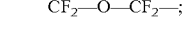

—(CF$_2$)$_{m'}$—SO$_2$—NH—SO$_2$(CF$_2$)$_{m'}$—; and,

—(CF$_2$)$_{m'}$—SO$_2$—CH(SO$_2$(CF$_2$)$_{m'}$—SO$_2$(CF$_2$)$_{m'}$—, wherein each m' is independently an integer from 1 to 12.

12. The polymer (I) according to claim 1, wherein the fluorinated polyfunctional compound of formula (II) is selected from the group consisting of:

(CF$_2$=CFCF$_2$—O)$_2$-PFPE (a);

CF$_2$=CF—O-PFPE-O—CF$_2$CF=CF$_2$ (b); and (CF$_2$=CFCF$_2$—O—CF$_2$CF$_2$SO$_2$)$_2$NH (c).

13. The polymer (I) according to claim 12, wherein the fluorinated polyfunctional compound of formula (II) is selected from compound (a) and compound (b), and wherein compounds (a) and (b) have PFPE units selected from the following groups:

—O—[CF(CF$_3$)CF$_2$O]$_{b1'}$(CFYO)$_{b2'}$— (1)

wherein:
Y, equal or different at each occurrence, is selected from a fluorine atom and a —CF$_3$ group;
b1' and b2', equal to or different from each other, are independently integers ≥0 such that the b1'/b2' ratio is comprised between 20 and 1000 and the (b1'+b2') sum is comprised between 5 and 250; should b1' and b2' be both different from zero, the different recurring units are generally statistically distributed along the perfluoropolyoxyalkylene chain, —O—[CF(CF$_3$)CF$_2$O]$_{c1'}$(C$_2$F$_4$O)$_{c2'}$(CFYO)$_{c3'}$— (2)

wherein:
Y, equal or different at each occurrence, has the same meaning as defined above;
c1', c2' and c3', equal to or different from each other, are independently integers ≥0 such that the (c1'+c2'+c3') sum is comprised between 5 and 250; should at least two of c1', c2' and c3' be different from zero, the different recurring units are generally statistically distributed along the perfluoropolyoxyalkylene chain, and —O—(C$_2$F$_4$O)$_{d1'}$(CF$_2$O)$_{d2'}$— (3)

wherein:
d1' and d2', equal to or different from each other, are independently integers ≥0 such that the d1'/d2' ratio is comprised between 0.1 and 5 and the (d1'+d2') sum is comprised between 5 and 250; should d1' and d2' be both different from zero, the different recurring units are generally statistically distributed along the perfluoropolyoxyalkylene chain.

14. A membrane comprising the polymer (I) of claim 1.

15. A method of manufacturing the polymer (I) according to claim 1, comprising polymerizing Monomer (A), Monomer (B) and the fluorinated polyfunctional compound of formula (II) in an aqueous emulsion in the presence of radical initiators.

16. The polymer (I) of claim 1, wherein monomer (A) is a compound of formula (I):

CF$_2$=CF—O—(CF$_2$CF(CF$_3$)O)$_m$—(CF$_2$)$_n$—SO$_2$X (I)

wherein m is 0 or 1, n is an integer between 0-10, and X is selected from F, OH, and O$^-$Me$^+$, wherein Me$^+$ indicates an alkali metal ion or an ammonium cation of formula NR$_4^+$ where each R independently represents a hydrogen atom or a monovalent organic radical selected from aliphatic radicals having from 1 to 8 carbon atoms and arylic or alicyclic radicals having from 3 to 8 carbon atoms.

17. The polymer (I) of claim 2, wherein polymer (I) comprises from 15 to 35% by weight of recurring units derived from monomer (A).

18. The polymer (I) of claim 3, wherein n is an integer between 2 and 4; p is 2 or 3; w is 1; R$_{F1}$ is —CF$_3$; y is 1 and R$_{F2}$ is F.

19. The polymer (I) according to claim 6, wherein polymer (I) comprises from 65 to 85% by weight of recurring units derived from monomer (B).

20. The polymer (I) according to claim 9, wherein polymer (I) comprises from 0.02 to 0.1% by weight of recurring units derived from fluorinated polyfunctional compound of formula (II).

* * * * *